Figure 1:
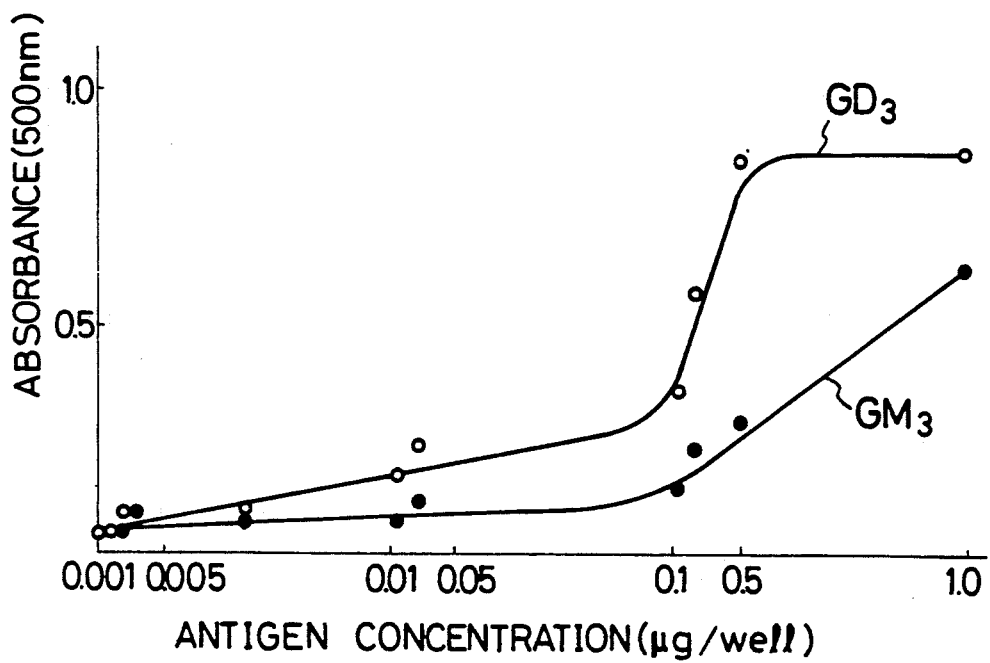

United States Patent [19]

Nagai et al.

[11] Patent Number: 5,141,864
[45] Date of Patent: Aug. 25, 1992

[54] MONOCLONAL ANTIBODY RECOGNIZING ALPHA 2→3 BONDS

[75] Inventors: Yoshitaka Nagai, Setagaya; Hideki Yamamoto, Kawasaki; Kinji Takada, Tokyo; Ito, Tokyo; Yoshiyasu Shitori, Tokyo, all of Japan

[73] Assignee: Mect Corporation, Tokyo, Japan

[21] Appl. No.: 270,205

[22] Filed: Nov. 14, 1988

[30] Foreign Application Priority Data

Nov. 17, 1987 [JP] Japan .................................. 62-290310

[51] Int. Cl.$^5$ ........................ C12N 5/20; C07K 15/28
[52] U.S. Cl. ................................ 530/387.5; 424/85.8; 424/85.91; 435/70.21; 435/172.2; 435/240.27; 530/388.85; 530/864; 935/104; 935/107
[58] Field of Search ...................... 424/85.8, 85.91, 88; 435/70.21, 172.2, 240.27; 530/387-389; 536/6

[56] References Cited

PUBLICATIONS

Hersey, P. et al., "Potentiation of Lymphocyte Responses by Monoclonal Antibodies to the Ganglioside GD3", *Cancer Research* 46:6083–6090, Dec. 1986.

"A Course of Experiments on the Biochemistry" pp. 1–2.

Eur. J. Immunol., vol. 16, 1986, pp. 951–956, "Production of oligosaccharide–binding monoclonal antibodies of diverse ...".

J. Exp. Med., vol. 150, Oct. 1979, pp. 1008–1019, "Production of monoclonal antibodies specific for two distinct ...".

*Primary Examiner*—John Doll
*Assistant Examiner*—Robert D. Budens
*Attorney, Agent, or Firm*—Oblon, Spivak, McClelland, Maier & Neustadt

[57] ABSTRACT

A hybridoma capable of producing a monoclonal antibody specific to a sialic acid containing glycolipid carrying N-acetylneuraminic acid residue having alpha 2→3 linkage is herein disclosed. The hybridoma can be generated by fusing (i) B cells or lymphocytes obtained by immunizing an animal with a sialic acid containing glycolipid carrying N-acetylneuraminic acid residue having alpha 2→3 linkage and (ii) myeloma cells. The monoclonal antibody produced by the hybridoma can be used for purifying gangliosides, for treating patients suffering from melanoma and for diagnosing sera.

5 Claims, 2 Drawing Sheets

MONOCLONAL ANTIBODY RECOGNIZING ALPHA 2→3 BONDS

BACKGROUND OF THE INVENTION

1. Field of the Invention

The present invention relates to a novel hybridoma, a method for generating the same and an anti-sialic acid-containing glycolipid monoclonal antibody produced by the hybridoma.

2. Description of the Prior Art

Hitherto, anti-sera are prepared by adsorbing the serum from an immunized animal on a variety of antigens. However, anti-sera contain a large number of antibody molecules originated from different B cells (polyclonal) and often cause cross reactions with other antibodies. Therefore, it is difficult to obtain anti-sera with excellent specificity.

Under such circumstances, in 1975, Köhlor developed a hybridoma which produces anti-sheep red blood cell antibody and which is generated by fusing spleen cells derived from an immunized animal and mouse myeloma cells to generate hybridomas. A clone which is a hybridoma originated from a single cell can be isolated from such hybridoma cells (so-called "cloning") because of its high proliferation potency. All the antibodies produced by such a cloned hybridoma are identical, have uniform specificity to an antigen and thus they recognize the same site of a specific antigen. In addition, the hybridomas can be stored in the frozen state, for instance, in liquid nitrogen. Therefore, the stable supply of the individual antibodies can be ensured. Thus, according to cell fusion technique, it becomes possible to obtain a monoclonal antibody highly specific to a specific antigen.

Antibodies are proteins which can recognize a molecule or substance referred to as "antigen" inherent thereto and can be bound to the same. The monoclonal antibody means an antibody having a site which specifically recognizes a specific antigen, in other words it recognizes only one antigenic determinant. Nowadays, various techniques for producing monoclonal antibodies and those for generating hybridomas capable of producing the same are well known in the art. In this respect, reference can be made to a recent publication "Monoclonal Hybridoma Antibodies: Techniques and Applications", edited by John G. Hurrell, 1983.

The glycolipid of mammalian cells belongs to the category of so-called sphingoglycolipid and comprises (a) a lipid structure referred to as ceramide composed of a long chain aminoalcohol called sphingosine to which a fatty acid is amido-bound and (b) various combination of sugars selected from the group consisting of glucose, galactose, N-acetylglucosamine, N-acetylgalactosamine, fucose and sialic acid which are bound to the structure through glycoside linkages. Among these, the glycolipids carrying sialic acid residue are called gangliosides.

Most of these compounds are generally located in the outer cellular membrane and it has been thought from recent investigations that gangliosides play an important role in the functions as a reception and response of recognition and information, receptor functions, differentiation, proliferation, malignant change, or behavior of cells.

Among these gangliosides, $GD_3$ gangliosides are known as the differentiated antigen of nerve cells and further identified as the cancer-related antigen of human melanoma cells.

Since the monoclonal antibody has high specificity to a specific antigen and thus can detect the same in high sensitivity as disclosed above, if a monoclonal antibody specific to the $GD_3$ gangliosides is obtained, it would be expected to apply such a monoclonal antibody to diagnosis of cancers (as a cancer marker) and immunological treatment as well as to the elucidation of sugar chain's role in cellular functions.

SUMMARY OF THE INVENTION

Accordingly it is a primary object of the present invention to provide a hybridoma capable of producing monoclonal antibodies specific to a specific antigenic determinant on the $GD_3$ ganglioside which is identified as the cancer associated antigen of human melanoma cells.

It is another object of the present invention to provide a method for generating such a hybridoma.

It is a further object of the present invention to provide a monoclonal antibody exhibiting specificity to the specific antigenic determinant on the $GD_3$ ganglioside.

The inventors of the present invention have conducted various studies to eliminate the aforesaid disadvantages and have found that in the cell fusion technique, the purified $GD_3$ ganglioside is used as an antigen to generate a hybridoma capable of producing a desired monoclonal antibody and thus the present invention has been completed.

According to an aspect of the present invention, a hybridoma is provided, which can produce a monoclonal antibody specific to sialic acid-containing glycolipids carrying N-acetylneuraminic acid residue having an alpha 2→3 linkage.

According to another aspect of the present invention, there is provided a method for generating a hybridoma capable of producing such a monoclonal antibody, which comprises fusing (i) B cells (B lymphocytes) obtained by immunizing an animal with, as an antigen, a sialic acid-containing glycolipid carrying N-acetylneuraminic acid residue having an alpha 2→3 bond and (ii) myeloma cells.

According to a further aspect of the present invention, there is also provided a monoclonal antibody specific to sialic acid-containing glycolipids carrying N-acetylneuraminic acid residue having an alpha 2→3 bond, as an epitope, the monoclonal antibody being produced by the aforesaid hybridoma.

BRIEF EXPLANATION OF THE ATTACHED DRAWINGS

Figure 2A:
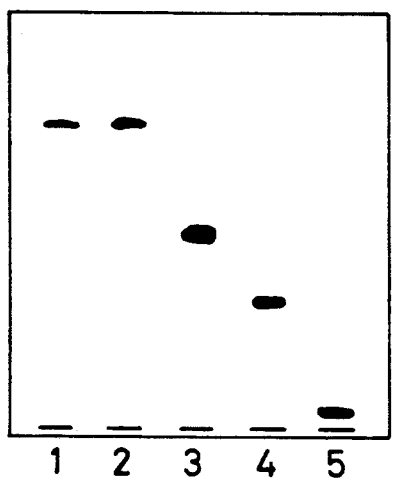
Figure 2B:
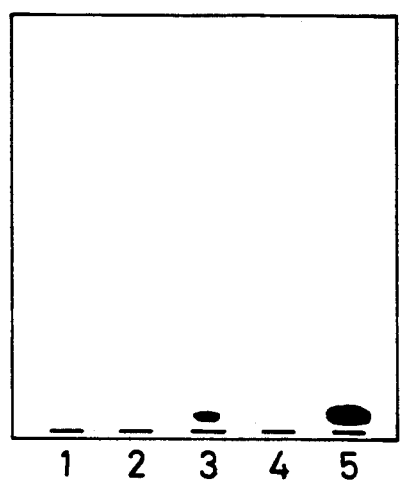
Figure 3A:
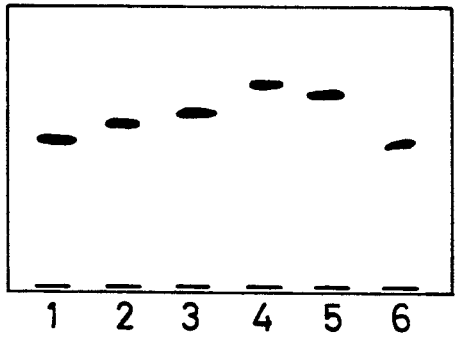
Figure 3B:
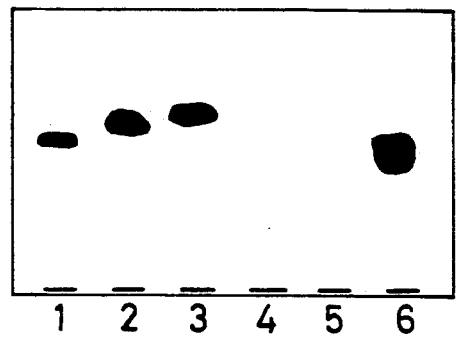
Figure 4:
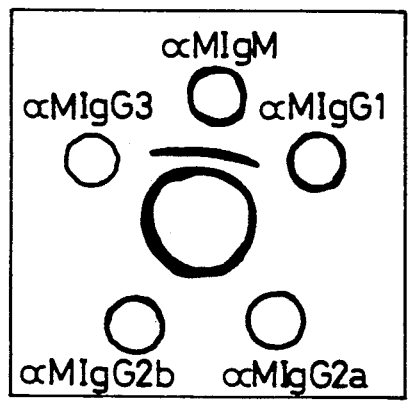

FIG. 1 shows the specificity of the monoclonal antibody of the present invention to antigens $GD_3$ and $GM_3$ determined according to enzyme-labeled antibody technique;

FIGS. 2 and 3 show antigen specificity of various kinds of gangliosides against the monoclonal antibody of the present invention, FIGS. 2(A) and 3(A) show results obtained by a TLC orcinol staining technique and FIGS. 2(B) and 3(B) show results obtained by a TLC immunostaining technique; and FIG. 4 shows a diagram used for classifying the monoclonal antibody of the present invention.

DETAILED EXPLANATION OF THE INVENTION

The present invention will hereunder be explained in more detail.

The hybridoma of the present invention can be generated by fusing B cells (B lymphocytes) obtained from an animal immunized with an antigen in accordance with the method of Kohlor & Millstein (see Nature 1975). The "antigen" herein used are, for instance, gangliosides containing N-acetylneuraminic acid residue having alpha 2→3 linkage preferably ganglioside glycolipids containing N-acetylneuraminic acid residue having alpha 2→3 linkage. Specific examples thereof are as follows:

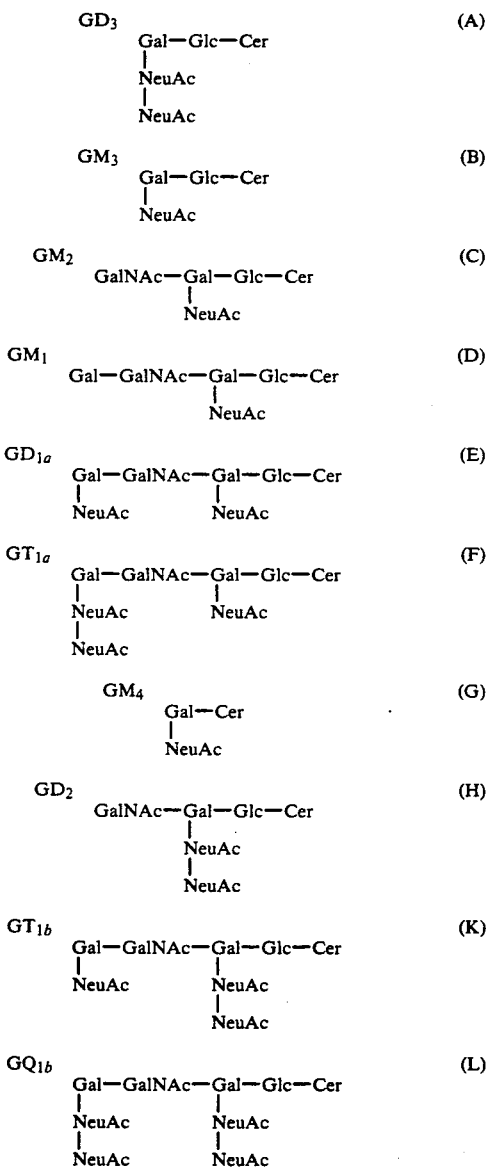

The monoclonal antibody produced by the hybridoma of the present invention recognizes N-acetylneuraminic acid having alpha 2→3 as the epitope or antigenic determinant and specifically reacts therewith. Therefore, the monoclonal antibody produced by the hybridoma shows particularly high reactivity with sialic acid containing glycolipids carrying N-acetyl- neuraminyl residue with alpha 2→3 linkage, in particular $GD_3$ and $GM_3$ gangliosides. In addition, the monoclonal antibody equally exhibits such a specificity to any these sialic acid containing glycolipids independent on the kinds of source animals.

"Animals" to be immunized with the antigen the aforementioned sialic acid containing glycolipid may be any kinds of animals. The specific examples thereof are rabbit, human, mouse and rat, preferably mouse and more preferably Balb/c mouse.

The B cells (B lymphocytes) which produce the monoclonal antibody of the present invention are preferably derived from spleen cells. On the other hand, "myeloma cells" used in the present invention may also be those derived from any animals such as human, mouse, rat and rabbit, preferably those derived from mouse and more preferably myeloma cells (X63-Ag8.653) derived from Balb/c mouse. These myeloma cells show extremely high proliferation potency so that the hybridoma generated by fusing them with the B cells can continously produce the monoclonal antibody of the invention.

The hybridoma of the present invention can be prepared by the method explained below in detail.

First of all, $GD_3$ ganglioside is injected into mice intraperitonealy, subctaneously or intravenously, preferably intravenously to immunize them. In this immunization, either incomplete adjuvants or complete adjuvants may be used as an adjuvant, i.e., an agent for immunological enhancement and specific examples thereof are oils, emulsifying agents, killed tubercule hacillus, killed Salmonella and mixture thereof, preferably killed *Salmonella minesota* for intraperitoneal or subctaneous injection and for intravenous injection. These antigen and adjuvant are preferably used in the form of a solution having approximately physiologically acceptable composition such as a solution in phosphate-buffered saline.

In this immunization, it should be noted that it is difficult to sensitize an animal to be immunized with the self-components and thus it is preferred, in principle to select the animal phenogenetically distant from that from which the antigenic substance is obtained. However, the immunization can also be performed in vitro in order to avoid such difficulties.

Then, the B cells and the myeloma cells are fused together. As an agent for cell fusion, there can be used polyethylene glycol and HVJ, preferably polyethylene glycol 6000. In addition, it is preferred to use HAT medium as the culture medium to easily isolate hybridoma cells from myeloma cells which remain unfused.

Thereafter, the resultant hybridoma cells are subjected to cloning operation such as methylcellulose technique, soft agarose technique or limiting dilution technique to isolate a desired single cloned hybridoma.

The antibody titer of the monoclonal antibody producing hybridoma thus generated can be examined in an ordinary manner to select hybridoma exhibiting high antibody titer. The hybridoma thus selected is then stored.

The monoclonal antibody produced by the hybridoma of the present invention can be used in detecting the glycolipid antigen naturally occurring in cancer tissues of human or animals. Therefore, the monoclonal antibody can be used in, for instance, ELISA and RIA assays which are usually adopted for the detection of cancer associated gangliosides. Moreover, the monoclonal antibody of the present invention may be used in affinity chromatography for purifying antigens capable of binding thereto. If the monoclonal antibody is labeled with a radioisotope, it may be used to detect tumuor or to identify the correct position thereof as well as it may be used in a high dose to treat patients suffering from tumour. It can also be linked to any chemotherapeutic agent to enhance the toxicity thereof to cancer cells. The monoclonal antibody of the present invention can be used for treating or diagnosing species having the antigen such as human and animals such as mouse. It is expected that the monoclonal antibody of the present invention can be applied to basic study of nerve cells and may be used for various clinical purposes.

The present invention will be explained in more detail with reference to the following non-limitative working Examples.

EXAMPLE

(A) Preparation of Antigen

(1) Extraction and Purification of $GD_3$ and $GM_3$ Gangliosides

After hog adrenal was homogenized in cold acetone and was dried, the dried product was extracted with chloroformmethanol in an ordinary manner.

The resultant sample was treated with an alkali and then $GD_3$ ganglioside was purified utilizing DEAE-Sephadex A-25 anion exchange resin and Iatrobeads column.

$GM_3$ ganglioside was prepared by centrifuging dog serum treated with heparin, washing the resultant sediment three times with phosphate-buffered saline (PBS(−)), lyophilizing it and then subjecting the product to extraction with chloroformmethanol. The purification thereof was performed in the same manner as above.

Gangliosides $GD_{1a}$, $GD_{1b}$ and $GQ_{1b}$ were available from DIATRON CO., LTD.; gangliosides Gal-Cer and Glc-Cer from Sigma Company and $GT_{1b}$ and $GM_2$ from FUNAKOSHI Company and these were used without further purification.

These ganglioside glycolipids were dissolved in chloroform-methanol (1:1 (v/v)) or ethanol and stored at −20° C.

(2) Animal

Six female Balb/c mice of 6 week-old were used for experiments after breeding under ordinary conditions.

(3) Preparation of Antigen Solution

Ganglioside $GD_3$ extracted from the hog adrenal and then purified and *Salmonella minesota* R 595 treated with acetic acid (weight ratio =1:4) and with diethylether were mixed in PBS(−) so that the concentration of GD3 ganglioside was 100 micrograms/ml and the resultant solution was used as the antigen solution.

(4) Culture Medium:

Culture Medium: Nissui RPMI 1640 (available from Nissui Seiyaku, Tokyo, Japan) was used as culture medium. To the medium, there were added kanamycin sulfate and fetal bovine serum (FBS) so that the final concentrations thereof were equal to 50 micrograms/ml and 10% respectively, prior to use.

HAT Medium: 0.0388 g of thymidine and 0.1361 g of hypoxanthine were dissolved in 100 ml of distilled water under heating and the resulting solution (a) was stored at 20° C. as a stock solution having a concentration 100 times higher than the desired one. Likewise, 0.0176 g of aminopterin was dissolved in 100 ml of distilled water by adding a small amount of IN sodium hydroxide aqueous solution, then this was diluted 10 times with RPMI 1640 culture medium and the resultant solution (b) was stored at −20° as a stock solution having a concentration 100 times higher than the desired one while shielding the light. HAT medium was prepared by adding 1/100 volume each of these two solutions to 10% FBS RPMI 1640 medium immediately before use.

Moreover, HT medium was prepared by simply adding 1/100 volume of the stock solution (a) containing hypoxanthin and thymidine to the same 10% FBS RPMI 1640 medium.

(5) Parent Cells

As the parent cells for cell fusion, there was used myeloma cells (C63-Ag8-6.5.3 cells) which were derived from Balb/c mice. These cells were subjected to subculture in RPMI 1640 medium to which 10% FBS was added while the generation of mutant was inhibited by adding 6-thioguanine to the medium so that the concentration thereof was equal to 3 microgram/ml.

(B) Preparation of Hybridoma

(1) Method of Immunization

Female Balb/c mice of 6 week-old were immunized by intravenously injecting the following immunogen solution in accordance with the following immunization schedule (amount injected was expressed in the amount of ganglioside): initially 5 micrograms, 10 micrograms at day 4, 15 micrograms at day 7, 20 micrograms at day 12 and 20 micrograms at day 79 after initiation. At day 3 after the final immunization, the mice were sacrificed to dissect away the spleen thereof and a suspension of individual spleen cells was prepared therefrom to subsequently use the same in cell fusion.

Immunogen Solution: 100 micrograms of $GD_3$ ganglioside extracted from the hog adrenal and purified and 400 micrograms of *Salmonella minesota* R 595 as an adjuvant were mixed in 1 ml of PBS (−) (free from $CA^{++}$ and $Mg^{++}$) and the resultant solution was then appropriately diluted to use as the immunogen solution.

(2) Cell Fusion

Fusion of the spleen cells obtained above and the mouse myeloma cells was performed according to the method of Kohlor and Millstein. More specifically, $1 \times 10^8$ spleen lymphocytes were fused with $2 \times 10^7$ myeloma cells in the presence of 50% polyethylene glycol (PEG 6000) in a culture medium.

(3) Selection and Breeding of Hybridoma

After the cell fusion, the resultant cells were cultured, in HAT medium (hypoxanthin, aminopterin and thymidine), at 37° C. in the presence of 5% $CO_2$.

The hybridoma thus generated had been deposited on Apr. 8, 1987, under the terms of the Budapest Treaty in American Type Culture Collection (ATCC) 12301 Parklawn Drive, Rockville, MA 20852 under the accession number of ATCC HB 9475.

(C) Estimation of the Reactivity of the Monoclonal Antibody with Gangliosides 96 well flat bottomed plate (available from Falcon Co., Ltd.) was pretreated with ethanol before using in experiments. 50 microliters each of the antigen solution (immunogem solution) which had been diluted with ethanol to adjust the concentration of $GD_3$ ganglioside to 20 micrograms/ml (optimum concn.) was pipetted into wells of the plate, then the solvent was evaporated off therefrom, 200 microliters each of 1% ovalbumin PBS(−) solution was introduced into the wells and they were allowed to stand for 30 minutes at room temperature. The plate was shaken while it as upside down to remove the solution, then 50 microliters each of the supernatant of the hybridoma culture medium, as the primary antibody, was added and the plate was allowed to stand for 1.5 hours at room temperature. Likewise, the primary antibody was removed from the wells, then the wells were washed three times by adding 150 microliters of PBS(−) solution and was allowed to stand for 30 minutes at room temperature after the addition of 100 microliters each of 1% ovalbumin PBS(−) solution. After the removal of this solution, 50 microliters each of secondary antibody diluted with 1% ovalbumin PBS(−) solution to its optimum concentration was added and was left to stand for 1.5 hours at room temperature. As in the case of the primary antibody, the wells were washed three times with PBS(−) solution and 100 microliters each of a reaction solution was added to cause reaction in the dark. The reaction solution was prepared by dissolving, into citrate-phosphate buffer (pH−5), o-phenylenediamine and hydrogen peroxide so that the concentrations thereof were 0.4 mg/ml and 0.01%, respectively. The reaction was stopped by the addition of 30 microliters each of 8N sulfuric acid solution and then the product was examined by colorimetry at 500 nm. As the secondary antibody, there were used goat anti-mouse $I_gG$, $I_gM$ and $I_gA$ antibodies labeled with horseradish peroxidase (HRP).

The results obtained are plotted on FIG. 1 wherein the filled circle represents ganglioside $GM_3$ and open circle represents ganglioside $GD_3$.

As seen from the results plotted on FIG. 1, the gangliosides $GD_3$ and $GM_3$ cause antigen-antibody reactions with the monoclonal antibody of the present invention in high sensitivity. Thus, both gangliosides $GD_3$ and $GM_3$ carry the antigenic determinant against the monoclonal antibody of the invention. In this connection, the ganglioside $GD_3$ shows reactivity with the monoclonal antibody higher than that of the ganglioside $GM_3$. Therefore, it is found that the ganglioside $GD_3$ has an epitope or antigenic determinant having more higher specificity to the monoclonal antibody of the present invention.

(2) TLC Immunostaining Technique

A silica gel thin layer chromatography (TLC(poly gram SIL G)) plate was cut into pieces of appropriate size and was spotted with a small drop of the solution of a glycolipid in chloroform-methanol (1:1 (v/v)). Depending on purposes, the plate was developed with a developing solution such as chloroform methanol-water (60/40/10; v/v), chloroform methanol 0.5%$CaCl_2$ solution (55/45/10; v/v) or chloroform methanol-2.5N $NH_4OH$ solution (60/40/9; v/v) and then was allowed to stand in 1% ovalbumine-1% polyvinyl pyrrolidone (K-30) PBS (−) solution at 4° C. overnight. Then, it was shaken for 2 hours at room temperature while dipping in the primary antibody solution. After sufficiently washing with PBS(−), it was dipped in 1% ovalbumin-1% polyvinyl pyrrolidone (K-30) PBS(−) solution at room temperature for 30 minutes. The plate was withdrawn therefrom, was dipped, for 2 hours, in the secondary antibody which was diluted to its optimum concentration with 3% polyvinyl pyrrolidone (K-30) PBS (−) solution with shaking then sufficiently washed with PBS(−) and a reaction solution was added thereto. The reaction solution was prepared by dissolving 4 mg of 4-chloro-1-napthol in 1 ml of methanol, adding 50 mmole of tris(hydroxymethyl)-aminomethane, 200 mmole of NaCl and 5 ml of a buffer (pH=7.4) and then adding hydrogen peroxide so that the concentration thereof was 0.01%. The reaction was stopped by washing the plate with water and then air-dried.

(3) Identification of Epitopes Specific to the Monoclonal Antibody of the Present Invention The results of qualitative tests and immunoreactions of various kinds of glycolipids obtained by TLC staining technique (orcinol staining) (A) and TLC immunostaining technique (B) are shown in FIG. 2. It is found, from the results shown in FIG. 2, that the ganglioside $GD_3$ of lane 5 has an antigenic determinant specific to the monoclonal antibody of the present invention.

Moreover, CDH (Gal-Glc-Cer) which was generated by acting *Vibrio cholera* sialidase on the ganglioside $GD_3$ of lane 3 is not detected when it was subjected to TLC immunostaining. This clearly indicates that the Gal-Glc-Cer (CDH) structure is not an antigenic determinant for the monoclonal antibody of the present invention. In addition, the band appearing on lane 3 of the TLC immunostaining indicates ganglioside $GD_3$ which is not affected by the aforesaid sialidase. In FIG. 2, CMH of lane 1 shows Gal-Cer and CMH of lane 2 is Clc-Cer and CTH of lane 4 shows Gal-Gal-Glc-Cer (CMH represents ceramide monohexoside; CDH represents ceramide dihexoside; CTH represents ceramide trihexodide).

Thus, it is found that these structures are not antigenic determinants for the monoclonal antibody of the present invention since they were not stained by TLC immunostaining technique.

As seen from the above, it is found that the antigenic determinant for the monoclonal antibody of the invention is N-acetylneuraminic acid residues.

| | | | |
|---|---|---|---|
| (1) | Lane 1: | CMH (Gal-Cer) (human brain) | 1 microgram |
| (2) | Lane 2: | CMH (Glc-Cer) | 1 microgram |
| (3) | Lane 3: | CDH (Cal-Glc-Cer) CDH (acting Vibrio cholera sialidase on $GD_3$. | 1 microgram |
| (4) | Lane 4: | CTH (Gal-Gal-Glc-Cer) | 1 microgram |
| (5) | Lane 5: | $GD_3$ | 1 microgram |

Likewise, the results obtained by staining a variety of gangliosides having N-acetylneuraminic acid residues by TLC immunostaining are summarized in Table I below.

TABLE I

| Results of TLC Immunostaining Test | |
|---|---|
| Antigen (100 pmole) | ATCC HB9475 |
| $GM_3$ | ++++++ |

TABLE I-continued

| Results of TLC Immunostaining Test | |
|---|---|
| GD$_3$ | +++++ |
| GD1a | ++ |
| GD1b | + |
| GT1b | ++ |
| GQ1b | +++ |
| :not detected. | |
| Samples | 578 nm |
| Control | 710 nm |
| Antibody Titer | |
| + | <20,000 |
| 20,000 <++ | <10,000 |
| 40,000 <+++ | <60,000 |
| 60,000 <++++ | <80,000 |
| 80,000 <+++++ | <100,000 |
| 100,000 <++++++ | |

(4) Identification of Epitope or Antigenic Determinant for the Monoclonal Antibody of the Present Invention As in FIG. 2, FIG. 3 shows the results of qualitative tests and immunoreactions of various kinds of glycolipids obtained by TLC staining technique (A) and TLC immunostaining technique (B). In FIG. 3, lanes 2 and 3 indicate the results of naturally occurring ganglioside, in other words N-acetylneuraminic acid having alpha 2→3 linkage. These lanes clearly show that the N-acetylneuraminic acid having alpha 2-33 linkage has strong specificity to the monoclonal antibody of the present invention.

In addition, lanes 4 and 5 show the results of chemically synthesized N-acetylneuraminic acid derivatives. These results indicate that the synthesized ganglioside does not have specificity to the monoclonal antibody of the present invention.

Taking into consideration synthetically both the present observations and those obtained in item (3), it can be concluded that the monoclonal antibody of the present invention recognizes the alpha 2→3 linkage of N-acetylneuraminic acid as its epitope or antigenic determinant.

Lanes in FIG. 3 will be detailed below:

| | | | |
|---|---|---|---|
| (1) | Lane 1: | GM$_3$ | 1 microgram |
| (2) | Lane 2: | N-Acetylneuraminic acid (NANA) alpha 2→3 Gal beta 1→1 Cer | 1 microgram |
| (3) | Lane 3: | N-Acetylneuraminic acid (NANA) alpha 2→3 Gal alpha 1→1 Cer | 1 microgram |
| (4) | Lane 4: | N-Acetylneuraminic acid (NANA) beta 2→3 Gal alpha 1→1 Cer | 0.5 microgram |
| (5) | Lane 5: | N-Acetylneuraminic acid (NANA) beta 2→3 Gal beta 1→1 Cer | 1 microgram |
| (6) | Lane 6: | CD$_3$ | 1 microgram |

(5) Qualitative Immunodiffusion Technique (Ouchterlony Technique)

FIG. 4 shows the results obtained by immunodiffusion technique. As seen from FIG. 4, the monoclonal antibody produced by the hybridoma of this invention is I$_g$M. In this method, anti-sera anti-MIgM, anti-MIgG1, anti-MIgG2a, anti-MIgG$_{2b}$ and anti-MIgG$_3$ were obtained from Miles Company.

(1) anti-MIgM
(2) anti-MIgG$_1$
(3) anti-MIgG$_{2a}$
(4) anti-MIgG$_{2b}$
(5) anti-MIg$_{G3}$ (6) The fact that the monoclonal antibody of the present invention is IgM is also demonstrated by the results obtained according to enzyme-labeled antibody technique, the results obtained in the method being summarized in Table II below.

TABLE II

| | Antibody Obtained from Hybridoma | |
|---|---|---|
| Secondary Antibody | + | − |
| anti-mouse IgM | 0.977 ± 0.079 | 0.066 ± 0.007 |
| anti-mouse IgG$_1$ | 0.131 ± 0.011 | 0.062 ± 0.011 |
| anti-mouse IgG$_{2a}$ | 0.137 ± 0.013 | 0.109 ± 0.010 |
| anti-mouse IgG$_{2b}$ | 0.121 ± 0.003 | 0.072 ± 0.006 |
| anti-mouse IgG$_3$ | 0.131 ± 0.007 | 0.046 ± 0.003 |

OD (Optical Density) at 500 nm
Antigen: GD$_3$ 500 ng/well
Third Antibody: goat anti-rabbit Ig-HRP

What is claimed is:

1. A hybridoma cell line having A.T.C.C. Accession No. HB 9475 producing a monoclonal antibody which immunologically binds gangliosides wherein said antibody recognizes the epitope N-acetylneuraminic acid having an α2→3 linkage.

2. A monoclonal antibody produced by the hybridoma cell line having A.T.C.C. Accession No. HB 9475 which immunologically binds to a ganglioside wherein said antibody recognizes the epitope N-acetylneuraminic acid having an δ2→3 linkage.

3. A monoclonal antibody as set forth in claim 2 wherein the ganglioside is GD$_3$ ganglioside or GM$_3$ ganglioside.

4. A monoclonal antibody as set froth in claim 2 wherein it is an IgM type immunoglobulin molecule.

5. A monoclonal antibody as set forth in claim 2, wherein the ganglioside is GD$_3$ ganglioside.

* * * * *

UNITED STATES PATENT AND TRADEMARK OFFICE
CERTIFICATE OF CORRECTION

PATENT NO. : 5,141,864

DATED : August 25, 1992

INVENTOR(S) : Yoshitaka Nagai et al.

It is certified that error appears in the above-identified patent and that said Letters Patent is hereby corrected as shown below:

On the Title Page, Item [75],

The fourth inventor's name is incomplete, should be, --Masayoshi Ito--.

Signed and Sealed this

Fourteenth Day of September, 1993

Attest:

BRUCE LEHMAN

Attesting Officer

Commissioner of Patents and Trademarks